US00PP12900P2

(12) United States Plant Patent
Bull et al.

(10) Patent No.: US PP12,900 P2
(45) Date of Patent: Sep. 3, 2002

(54) APPLE TREE NAMED 'BULL MACINTOSH'

(75) Inventors: Leslie lee Bull; Linda lou Bull, both of Casnovia, MI (US)

(73) Assignee: International Plant Management, Inc., lawrence, MI (US)

( * ) Notice: Subject to any disclaimer, the term of this patent is extended or adjusted under 35 U.S.C. 154(b) by 0 days.

(21) Appl. No.: 09/542,613

(22) Filed: Apr. 4, 2000

(51) Int. Cl.[7] ..... A01H 5/00
(52) U.S. Cl. ..... Plt./165
(58) Field of Search ..... Plt./165

*Primary Examiner*—Bruce R. Campell
*Assistant Examiner*—Susan B. McCormick

(57) ABSTRACT

A new and distinct variety of MacIntosh apple tree, 'Bull MacIntosh,' originating as a whole tree mutation of the *Malus sylvestris* variety of 'Starling' (U.S. Plant Pat. No. 7,617). This new variety is unique from its parent and other MacIntosh cultivars because the fruit begins coloring 35 days earlier than the parent and 45 days earlier than other MacIntosh cultivars. The new variety ripens to a 100% red blush as opposed to its parent, which ripens to a red striped coloration. The 'Bull MacIntosh' cultivar reaches maturity with the 'Starling' cultivar and 10 to 15 days ahead of other MacIntosh clones.

4 Drawing Sheets

FIELD OF THE INVENTION

A new and distinct variety of MacIntosh apple tree originating as a whole tree mutation of the *Malus sylvestris* variety of 'Starling' (U.S. Plant Pat. No. 7,167), hereinafter referred to as the 'Bull MacIntosh'. This new sport is unique from its parent because the fruit starts coloring 35 days earlier as a red blush over a faint red stripe. The color develops as a solid, bright red blush with no striping. The color finishes to a virtually 100% solid, bright red blush.

DESCRIPTION OF PRIOR ART

The new variety, 'Bull MacIntosh', differs from its parent and other MacIntosh varieties in the following characteristics:

A. The new variety develops color 35 days earlier than its parent, 'Starling' (U.S. Plant Pat. No. 7,167) and 'Greenslade' (U.S. Plant Pat. No. 2,982). It develops color 45 days earlier than 'Hartenmac NS 219' (U.S. Plant Pat. No. 10,770), 'Pioneer Mac' (U.S. Plant Pat. No. 7,002). 'Apple Tree' Chick (U.S. Plant Pat. No. 5,508), Mutation of Summerland Red McIntosh apple tree (U.S. Plant Pat. No. 4,383) and 'Raikes' (U.S. Plant Pat. No. 3,390).

B. The fruit on the new variety matures with 'Starling', 10 days ahead of 'Apple Tree' Chick, 'Raikes', Mutation of Summerland Red McIntosh apple tree, 'Hartenmac NS 219', and 'Greenslade' and 15 days ahead of 'Pioneer Mac'.

C. The color finishes as a 100% solid, bright red blush with no striping.

SUMMARY OF THE INVENTION

This new and distinct variety of MacIntosh apple tree was discovered in 1997 as a whole tree mutation of 'Starling', in an orchard planted in 1984 on the Leslie and Linda Bull farm near Casnovia, Mich. The new variety was noticed because the fruit started coloring the first week in July, about 5 to 6 weeks ahead of all other 'Starling' fruit in the orchard.

Observations during the next two seasons confirmed the early coloring and also that the fruit colored with a solid, bright red blush with no striping as opposed to 'Starling', which colors with a distinct stripe. The mature fruit of the new variety finishes to a 100% solid, intense bright red color with no striping.

In August of 1997, buds were taken from the original tree and trees for further testing were asexually produced into 200 trees. This new cultivar has been reproduced on Malling 9-337 and Malling 9 NIC 29 rootstocks and remains true to the description herein contained. The new variety had not been grown on its own root.

BRIEF DESCRIPTION OF THE DRAWINGS

The accompanying photographs show typical specimens of the new variety as depicted in color as nearly true as is reasonably possible in color illustrations of this character. These specimens were obtained at the Leslie and Linda Bull farm in Casnovia, Muskegon County, Mich., 49318.

BOTANICAL DESCRIPTION OF THE PLANT

Figure 1:
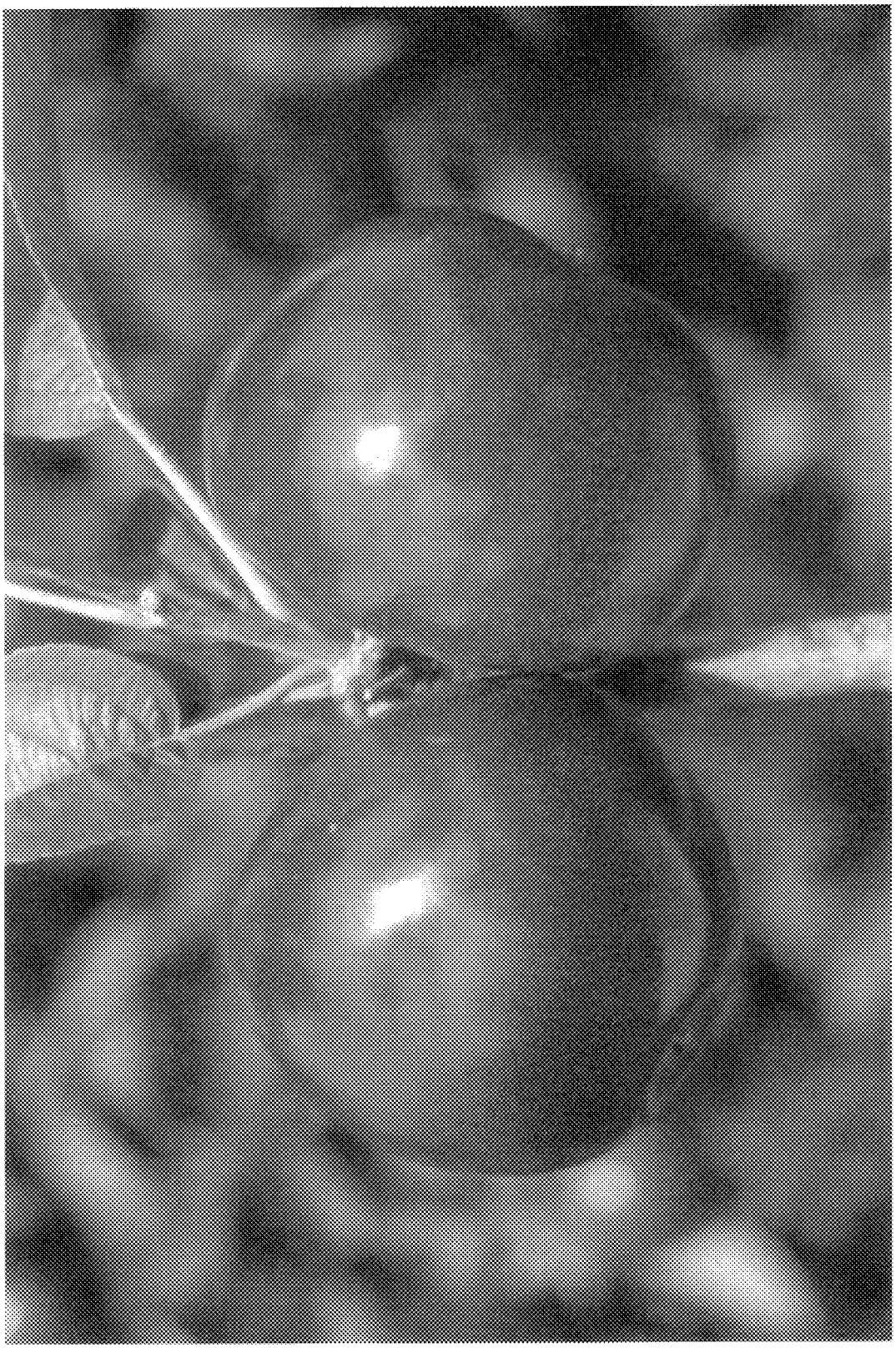
FIG. 1 illustrates the fruits of the new variety at maturity.
Figure 2:
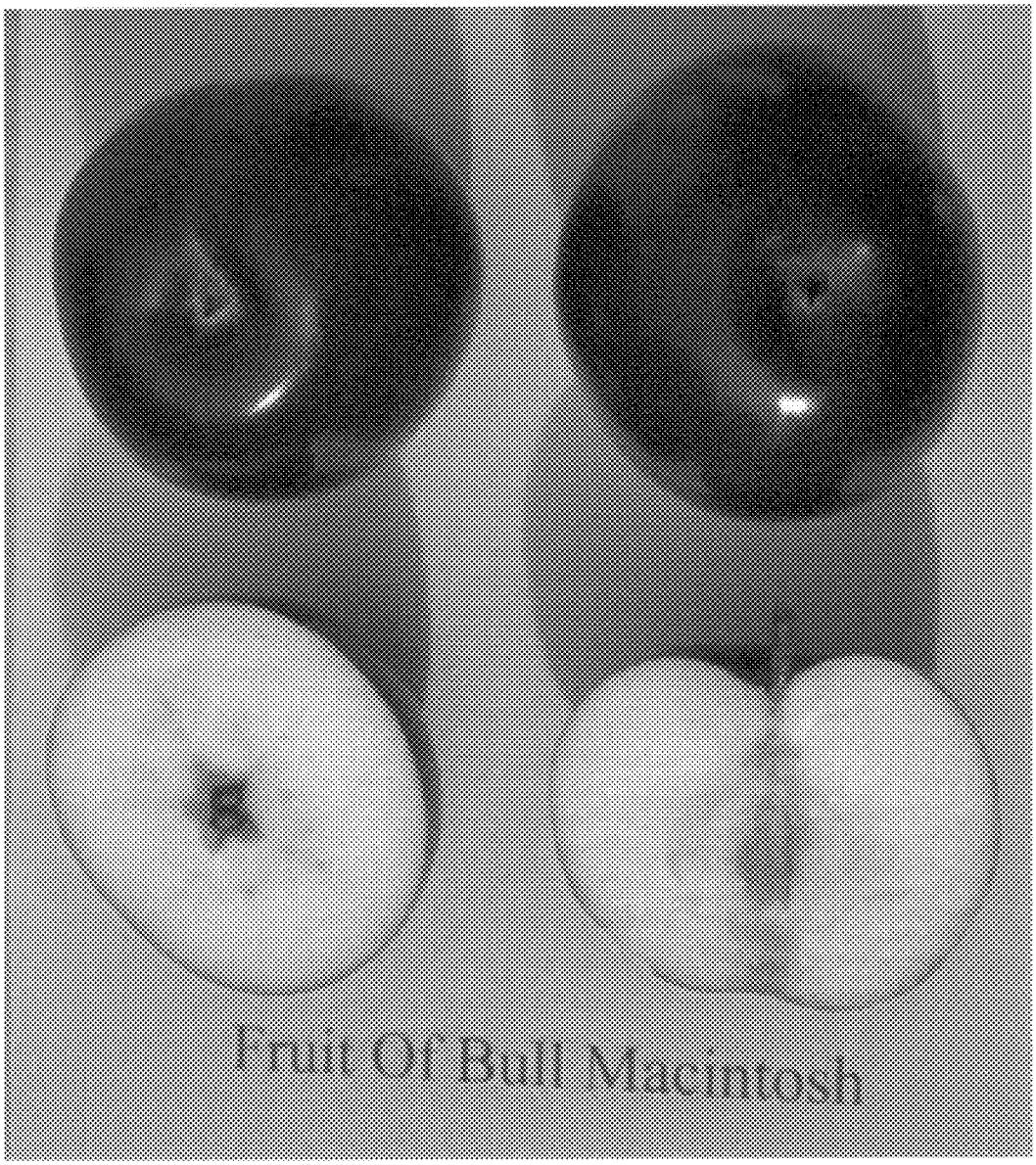
FIG. 2 illustrates a section of the new variety at maturity.
Figure 3:
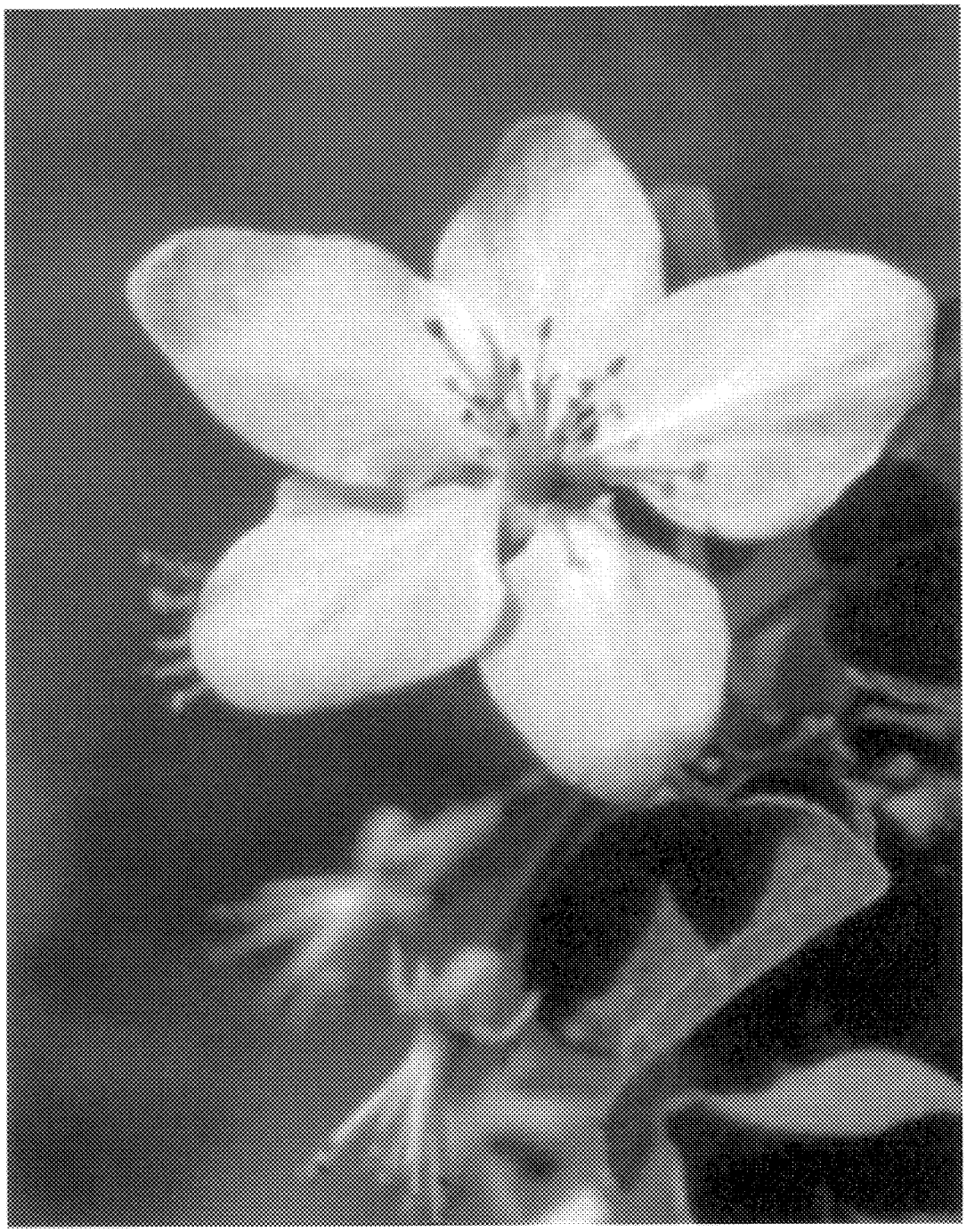
FIG. 3 illustrates a blossom of the new variety.
Figure 4:
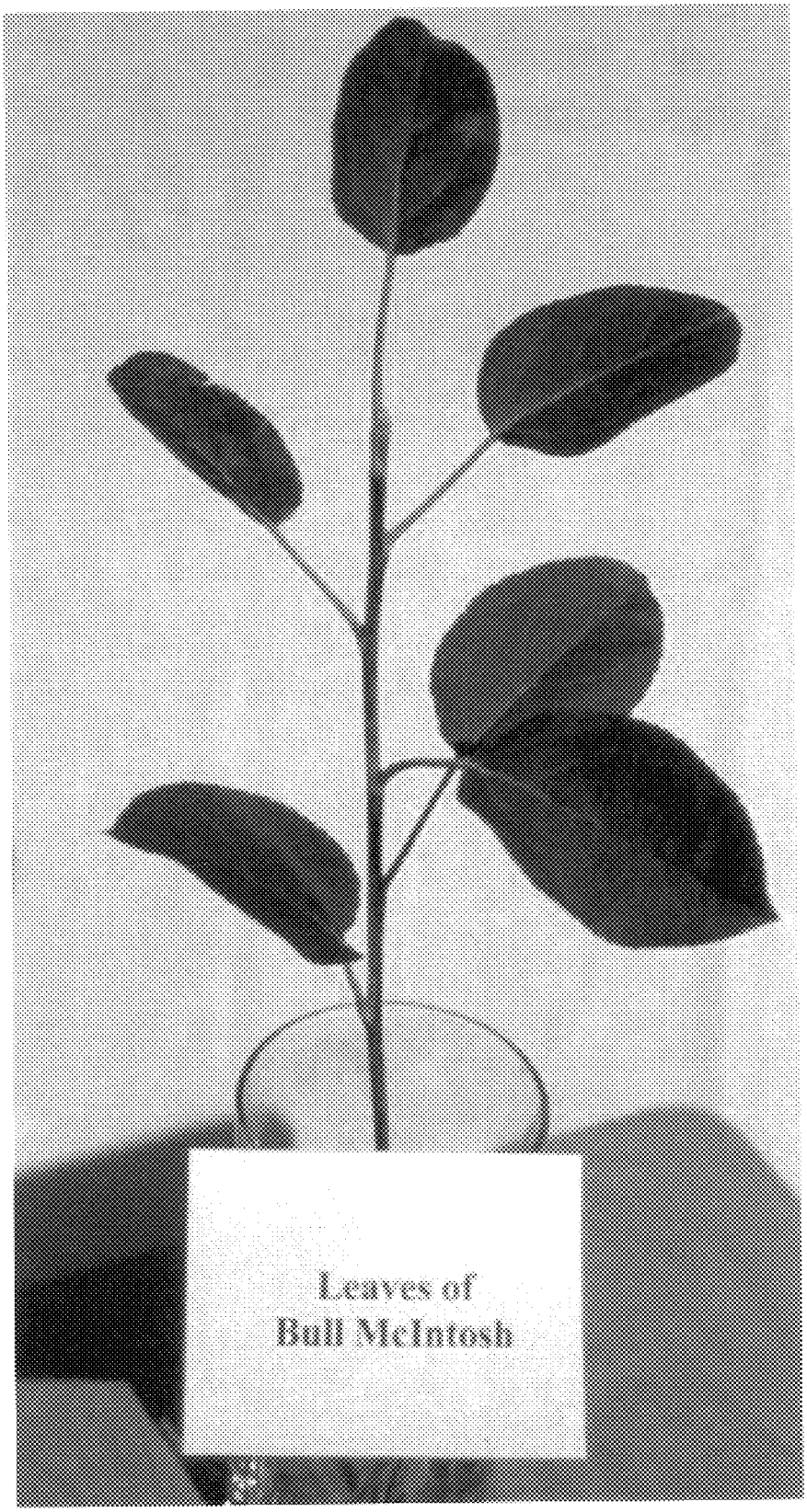
FIG. 4 illustrates the foliage of the new variety.

A detailed description of the Bull MacIntosh cultivar follows using The Royal Horticultural Society of London Colour Chart for color identification except where general color terms are sufficient.

Classification: PLT/165.

Parentage: A whole tree mutation of 'Starling', (U.S. Plant Pat. No. 7,167). Locality of the original discovery and observations is Leslie & Linda Bull Orchards, 16530 Hall Road, Casnovia, Muskegon County, Mich., 49318.

Tree:

*Age.*—16 years.

*Size.*—Large, height 6 m, width 4 m.

*Vigor.*—Vigorous, yearly growth averages 1 m.

*Density.*—Medium.
*Form.*—Upright, spreading.
*Production.*—Very productive, averaging 800 bushels per acre.
*Growth type.*—Non-spur.
*Bearing.*—Annual.

Trunk:
*Size.*—45 cm in diameter at 100 cm above ground level.
*Surface.*—Smooth.
*Bark color.*—Grey Group 201 B.
*Lenticels.*—Length 2 cm, width 0.5 cm.
*Lentical color.*—Grayed White 156 D.
*Lenticel density.*—2 per $cm^2$.

Branches:
*Diameter 1 year.*—11 mm.
*Diameter 2 year.*—22 mm.
*Surface.*—Smooth.
*Branch color.*—Greyed-Orange 172 B.
*Form.*—Profuse branching.
*Average angle.*—60°.
*Buds.*—Alternate, tightly applied to branch.
*Lenticels.*—Small, few, round to elongate.
*Lentical color.*—White 155 A.

Leaves:
*Size.*—Length 85 mm, width 50 mm.
*Form.*—Ovate.
*Texture.*—Crisp, tough.
*Leaf thickness.*—0.3 mm.
*Base.*—Rounded.
*Apex.*—Acute to slightly mucronate.
*Margin.*—Crenate.
*Pubescence.*—None on adaxial surface, fine pubescence on abaxial surface.
*Leaf color.*—Adaxial: Yellow-Green Group 147 A, Abaxial: Yellow-Green Group 146 B.
*Venation.*—Pinnate, 8–10 veins, mainly alternate.
*Vein color.*—Adaxial: Green 148 C. Abaxial: Green 148 D with some Red 53 B.
*Stipules.*—2, small, at base of petiole on most older leaves; length: 5 mm.
*Stipule color.*—Green 146 D.
*Petiole.*—Length 35 mm, diameter 2 mm.
*Petiole color.*—Yellow Green Group 146 C with Red Group 53 B.

Flower buds at popcorn stage:
*Pedicel.*—Length: 15 to 20 mm, diameter 2 mm.
*Pedicel color.*—Green 146 D.
*Bud.*—Length 9 mm, width 7 mm.
*Bud color.*—Red 56 C blush with background of White 155 D.

Flowers:
*Bloom timing.*—Early season.
*Blooming period.*—April 13 to 20 in Casnovia, Muskegon County, Mich.
*Pollination requirements.*—Viable pollen from another early season blooming apple variety such as 'Idared', 'Spartan' or 'Manchurian' crabapple.
*Number of flowers per cluster.*—3 to 5.
*Fragrance.*—Very fragrant.
*Corolla diameter.*—25 to 34 mm.
*Stamens.*—20 to 25 in number, color White 155 D.
*Anther color.*—Yellow 14 B.
*Pollen.*—Profuse.
*Ovary.*—Pubescent, color Grayed Green 193 A.
*Pistil.*—Slightly lower than anthers in a majority of blossoms.
*Sepals.*—5 in number, length 4 mm, width 2 mm, pubescent, color Grayed Green 193 A.
*Petals.*—5 in number, length 11 mm, width 6 mm, slightly overlapping.
*Petal shape.*—Ovate, base rounded to cuneate at junction with receptacle, apex rounded, margin very sightly ruffled.
*Petal color.*—Adaxile: White 155 D. Abaxile: White 155 D.
*Petal texture.*—Soft.

Fruit:
*Maturity when described.*—Firm ripe.
*Date of picking.*—September 1, in Casnovia, Muskegon County, Mich., generally harvested in one picking.
*Size.*—Axial diameter 5.2 to 5.8 cm, transverse diameter 7.0 to 8.5 cm.
*Form.*—Uniform, symmetrical, regular, globular to ovate.
*Cavity.*—Obtuse, shallow, depth 6 mm, breadth 6 mm.
*Basin.*—Symmetrical, abrupt at base, wide, depth, 5 mm, width 5 mm.
*Calyx.*—Closed, segments persistent, erect, outer and inner surfaces pubescent.

Skin:
*Thickness.*—Thin.
*Texture.*—Very smooth, glossy with medium cuticle wax.
*Tendency to crack.*—None.
*Lenticels.*—White, inconspicuous, small, few in number.
*Color.*—Solid blush 100% Red Group 53 A, with no striping.
*Ground color.*—Yellow-Orange Group 144 B.

Flesh:
*Aroma.*—Sweet, aromatic.
*Color.*—Grayed-White 155 A.
*Texture.*—Firm, tender, fine, crisp.
*Eating quality.*—Best.

Core:
*Bundle area.*—Medium to ovate, cordate, symmetrical at base.
*Bundle.*—Inconspicuous, green, alternate above stamens.
*Capillary area.*—Distinct, medium size.
*Calyx tube.*—Urn shaped, closed.
*Depth of tube to shoulder.*—16 mm.
*Styles.*—Distinct, pubescent.
*Stamens.*—One distinct whorl, small.
*Axillary cavity.*—Wanting.
*Seed cells.*—Walls thin, tough, length 17 mm, breadth 6 mm.
*Longitudinal section.*—Broadly ovate.

Seeds:
*Number perfect.*—6 to 10.
*Number in one cell.*—1 to 2
*Length.*—6 mm.
*Breadth.*—3 mm.
*Form.*—Obtuse, non-tufted.
*Color.*—*Fan* 4, Grayed-Orange, 175 A.

Stem:
*Length.*—16 mm.
*Width.*—3 mm.
*Color.*—Yellow Green 151 A with blush of Grayed Red 178 A.

Use: Processing, fresh market, dessert.
Shipping quality: Good, subject to stem puncture.

Keeping quality: Excellent, 90 to 120 days in common storage, 6 months in controlled atmosphere storage.

Tree winter hardiness: Above average for an apple variety. Tree is hardy to −20° to −35° F.

Bud winter hardiness: −15° to −20° F., depending on the stage of development of the bud.

Drought tolerance: Average for an apple variety. Normal requirements average ½" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

We claim:

1. A new and distinct variety of apple tree, *Malus sylvestris*, substantially as herein shown and described, characterized particularly as to novelty by the unique combination of a vigorous, upright, spreading, medium density, regular bearing tree, producing fruits that develop color 35 days before the parent and finish coloring as a 100% bright red blush with no striping at maturity which occurs at the same time as the parent.

* * * * *